United States Patent
Brown

[19]

[11] Patent Number: 5,873,365
[45] Date of Patent: Feb. 23, 1999

[54] KINESIOLOGIC MOUTHPIECE AND METHOD

[76] Inventor: Thomas J. Brown, 1146 Guinevere, Liberty, Mo. 64068

[21] Appl. No.: 695,390

[22] Filed: Aug. 12, 1996

[51] Int. Cl.[6] .................................................. A61C 5/14
[52] U.S. Cl. ............................................. 128/859; 128/861
[58] Field of Search ............................ 128/848, 859–862; 2/2; 602/902

[56] References Cited

U.S. PATENT DOCUMENTS

| | | | |
|---|---|---|---|
| 3,532,091 | 10/1970 | Lerman | 128/861 |
| 3,682,164 | 8/1972 | Miller | 128/861 |
| 5,235,991 | 8/1993 | Minneman | 128/859 |
| 5,339,832 | 8/1994 | Kittelsen | 128/859 |
| 5,447,168 | 9/1995 | Bancroft | 128/859 |

*Primary Examiner*—Michael A. Brown
*Attorney, Agent, or Firm*—Litman, McMahon & Brown, L.L.C.

[57] ABSTRACT

A kinesiological mouthpiece includes a strap assembly with a bridge, a pair of extensions extending generally rearwardly and outwardly from the bridge and a pair of wings extending generally rearwardly from the extensions. The strap assembly is flexible for forming in a generally U-shaped use configuration. The wings are displaced at a different level from the bridge whereby the bridge can be positioned generally between the lower teeth and the lower lip with the wings approximately located on bite lines of the back teeth. A pair of bitepad assemblies are rotatably and longitudinally-adjustably mounted on the wings and each includes a bitepad with upper and lower contact surfaces for contacting by the back teeth. An occlusal support method includes the steps of providing a strap assembly, placing the strap assembly around the lower teeth, adjustably and rotatably mounting a pair of bitepad assemblies on the strap assembly, placing the bitepad assemblies between the back teeth and relieving tension on the temporomandibular joint.

20 Claims, 4 Drawing Sheets

KINESIOLOGIC MOUTHPIECE AND METHOD

BACKGROUND OF THE INVENTION

1. Field of the Invention

The present invention relates generally to kinesiologic mouthpieces for occlusal support and in particular to a kinesiologic mouthpiece which provides spacing between the rear teeth to avoid bruxism (teeth clenching) and teeth grinding.

2. Description of the Related Art

Kinesiology is commonly applied to various activities, including sports, for optimizing the performance of the participants. For example, the proper alignment and orientation of the skeletal structure is considered a significant factor in optimizing athletic performance. Thus, athletic training for many sports emphasizes correct posture, positioning, stance, etc. for developing effective techniques.

Another factor common to many types of sports is the need for strength. Greater power and endurance, and the ability to apply same with proper techniques, are significant factors in determining the outcome of many athletic contests. Athletes therefore typically spend large amounts of time practicing their techniques and engaging in physical training to increase strength, speed, endurance, coordination, reflexes, etc.

A number of factors effect an athlete's ability. Factors such as genetic makeup are beyond the athlete's control. However, other performance-effecting factors, such as diet and conditioning, are within the athlete's control and receive considerable attention in athletic training programs.

Mandibular position and orientation of the temporomandibular joint ("TMJ") have been linked to muscular strength and athletic performance. For example, objective evidence of this correlation was reported in Smith, S. D. "Muscular Strength correlated to Jaw and the Temporomandibular Joint". *N.Y. State Dental Journal* 44(7):279–82, 1978. Various problems associated with bursitis (teeth clenching), grinding and temporomandibular joint ("TMJ") misalignment have been reported, and include chronic headaches and other physiological problems. See, for example:

Gelb, H., and Tarte, J. A two year clinical dental evaluation of 200 cases of chronic headache: The crania cercicalmandibular syndrome. *JADA* 91:1230–1236, Dec. 1975;

Gelb, H., and Berstein, I. Clinical evaluation of 200 patients with TMJ syndrome: *J of Pros. Dent.* 49(2) :234–243, Feb. 1983.

A partial solution to TMJ syndrome and dysfunction has been achieved through the use of mandibular orthopedic repositioning appliances ("MORA"), and the benefits of such devices in athletics have been reported in the literature, such as:

Jakush, J. Divergent views: can dental therapy enhance athletic performance? *JADA* 104:292–298, Mar. 1982.

Kaufman, R. S. Case reports of TMJ repositioning to improve scoliosis and the performance of athletes. *N.Y. State Dent. J.* 40(4):206–209, 280, Apr. 1980.

Kaufman, A. and Kaufman, R. Usefulness of the MORA to reduce headaches on the U.S. Olympic Luge Team. *Basal Facts.* In Press.

Kaufman, A. and Kaufman, R. Effects of the Mora on members of a football team. *Quintessense International* 6:677–681, Jun. 1983.

The effects of TMJ positioning on muscular strength were also reported in:

Williams, M. O.: Chaconis, S. J.: and Bader, P. The effects of mandibular position on appendage muscle strength. *J. of Pros. Dent.* 49(4):560–567, Apr. 1983.

Mouthguards are commonly utilized in sports for protecting the head, neck and teeth, as discussed in:

Stenger, J., Lawson E., Wright, J.; and Rickets, J. Mouthguards: Protection against shock to head, neck and teeth. *JADA* 69:273, 1964.

In addition to providing protection against shock, TMJ positioning can be accomplished with mouthpieces, such as the MORA's described in the Gelb, et al. article noted above.

The negative effects of teeth grinding and clenching include tension, stress, lack of concentration, fatigue, etc., all of which can adversely effect performance. In athletic contests it is particularly desirable to enhance performance and eliminate physical characteristics which could hamper same. In many athletic competitions relatively small advantages can control the outcome. For example, slight advantages in speed, strength and coordination can be sufficient to tip the balance in favor of a particular player or team. Conversely, if a player or a group of players on a team are suffering from stress, fatigue, lack of concentration, etc., the player or team will be likely to lose to an opponent which is free from such negative attributes.

Proper mandibular alignment is an important factor in enhancing performance through the elimination of teeth grinding and teeth clenching. Studies have concluded that sports performance can be enhanced by providing proper mandibular positioning and thus eliminating teeth grinding and clenching.

Mouthpieces are commonly used in a wide variety of sports and various styles have been devised to meet the requirements of particular sports. For example, mouthpieces which provide protection for the upper and lower lips and upper and lower sets of teeth are commonly used in contact sports. However, such mouthpieces have the disadvantage of interfering with speaking and breathing, and can be uncomfortable. Another disadvantage with this type of mouthpiece is that obtaining a proper fit for a particular player's mouth with standard sizes can be difficult. Thus, various sizes of mouthpieces must be provided in an attempt to accommodate as many individuals as possible, although such fitting procedures are generally somewhat of a compromise.

The present invention addresses these shortcomings of prior art mouthpieces by providing a kinesiological mouthpiece which can be adjusted for optimum fit.

SUMMARY OF THE INVENTION

In the practice of the present invention, a kinesiological mouthpiece is provided which includes a strap assembly having a bridge, a pair of extensions extending rearwardly, outwardly and upwardly therefrom and a pair of wings extending generally rearwardly from the extensions. The strap assembly is designed to fit over the lower teeth with the strap assembly located generally between the lower teeth and the lips. A pair of bitepad assemblies are rotatably and longitudinally-adjustably mounted on the wings and each includes a bitepad for location between the upper and lower back teeth. An occlusal support method is provided which includes the steps of providing a strap assembly; placing the strap assembly around the lower teeth; adjustably and rotatably mounting a pair of bitepad assemblies on the strap assembly; placing the bitepad between the lower teeth; and relieving tension on a temporomandibular joint.

OBJECTS AND ADVANTAGES OF THE INVENTION

The principle objects and advantages of the present invention include: providing a kinesiological mouthpiece; providing such a mouthpiece which facilitates proper mandibular closure; providing such a mouthpiece which facilitates proper alignment and positioning of the temporomandibular joint; providing such a mouthpiece which prevents teeth grinding and clenching; providing such a mouthpiece which provides a fissure between the upper and lower teeth; providing such a mouthpiece which can facilitate an increase in sports performance; providing such a mouthpiece which reduces the effects of teeth clenching and grinding in athletes; providing such a mouthpiece which can enhance physical performance; providing such a mouthpiece which can enhance concentration; providing such a mouthpiece which is adjustable in fit to accommodate its wearers; providing such a mouthpiece which is economical to manufacture, efficient in operation, capable of a long operating life and particularly well adapted for the proposed usage thereof; providing such a mouthpiece which is relatively comfortable; providing such a mouthpiece which is relatively concealed in use; providing such a mouthpiece which avoids substantial interference with breathing and speaking; and providing such a mouthpiece which is usable by a wide range of athletes and others.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE PREFERRED EMBODIMENTS

I. Introduction and Environment

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. Said terminology will include the words specifically mentioned, derivatives thereof and words of a similar import.

Referring to the drawings in more detail, the reference numeral 2 generally designates a kinesiological mouthpiece embodying the present invention. The mouthpiece 2 generally comprises a strap assembly 4 which is positioned, for example, between the lower teeth and lip and a pair of bitepad assemblies 6, each of which is mounted on the strap and placed between the upper and lower molars on a respective side of the mouth. As will be explained in more detail hereinafter, the mouthpiece 2 provides occlusal support with a slight gap between the back teeth, which forms a temporomandibular joint 8.

II. Strap Assembly 4

Figure 1:
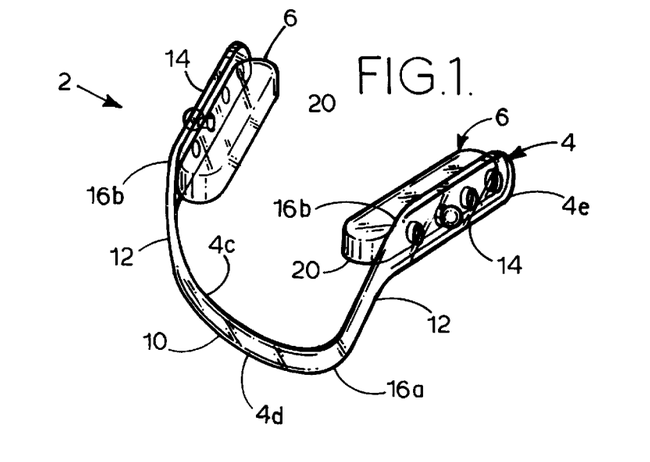
FIG. 1 is an upper, front, left side perspective view of a kinesiologic mouthpiece embodying the present invention.
Figure 2:
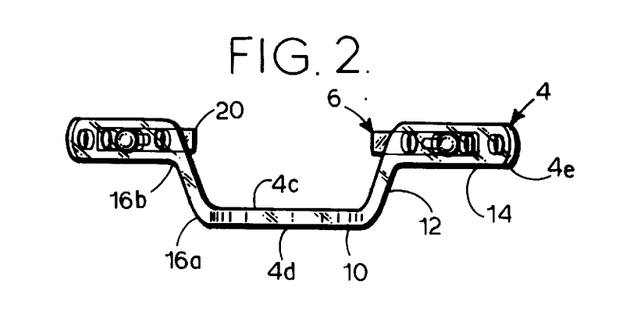
FIG. 2 is a front elevation view thereof.
Figure 3:
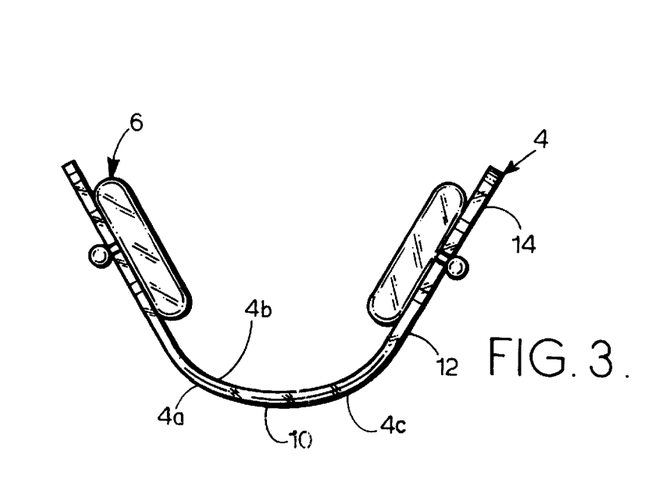
FIG. 3 is top plan view thereof.
Figure 4:
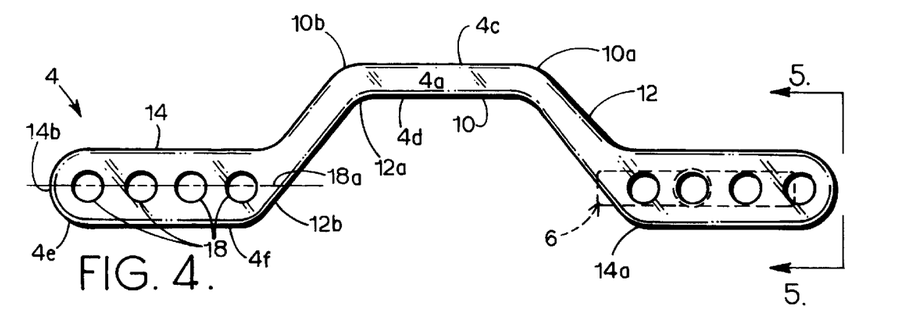
FIG. 4 is a front elevational view of a strap assembly thereof, shown in a flattened position, with a bitepad assembly thereof shown in dashed lines.
Figure 5:
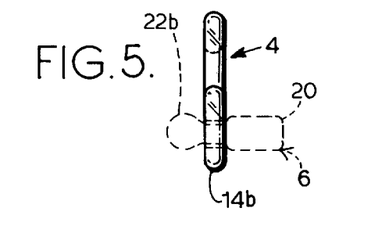
FIG. 5 is an end elevational view of the strap assembly, with the bitepad assembly shown in dashed lines.

The strap assembly 4 includes first and second faces 4a,b; rounded upper and lower edges 4c,d; and rounded corners 4e. The strap assembly further includes a bridge 10 with opposite sides 10a,b; a pair of extensions 12 each having a front end 12a connected to a respective bridge side 10a and a back end 12b; and a pair of wings 14 each including a front end 14a connected to a respective extension back end 12b and a free back end 14b. In a flat configuration as manufactured, the bridge 10 is generally parallel to the wings 14 but offset therefrom (FIG. 4), with the extensions 12 forming front and back obtuse-angled connections 16a,b at their respective connections to the bridge 10 and the wings 14.

Each wing 14 includes a plurality (e.g., four are shown) of receivers 18 positioned in longitudinally-spaced relation along a receiver line 18a which extends generally parallel to the upper and lower edges 4c,d at the wings 14. The receivers 18 extend between and are open at the strap faces 4a,b.

The strap 4 preferably has rounded corners, edges, etc. for comfort, for example, along the edges 4c,d and at the wing back ends 14b which form corners 4e.

III. Bitepad Assemblies 6

Figure 6:
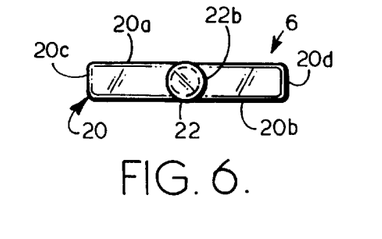
FIG. 6 is a side elevational view of the bitepad assembly.
Figure 7:
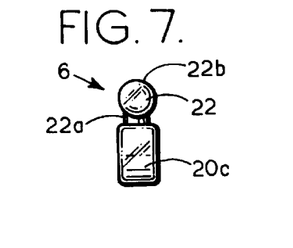
FIG. 7 is an end elevational view of the bitepad assembly.
Figure 8:
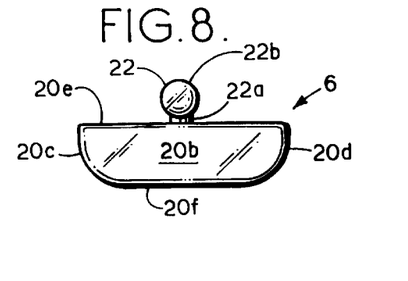
FIG. 8 is a top plan view of the bitepad assembly.

Each bitepad assembly 6 includes a bitepad 20 with first and second contact surfaces 20a,b; front and back rounded ends 20c,d; and inner and outer edges 20e,f. Each bitepad also includes a pin subassembly 22 comprising a shank 22a extending outwardly from a respective bitepad outer edge and a ball 22b mounted on the outer end of each pin shank in spaced relation from a respective bitepad outer edge 20f.

As with the strap assembly 4, the bitepad assemblies 6 preferably have rounded edges 20c,d and ends 20e,f for comfort.

Figure 8A:
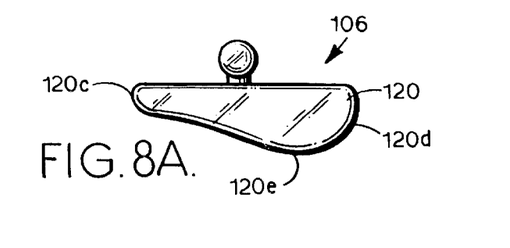
FIG. 8a is a plan view of a modified bitepad assembly.
Figure 9:
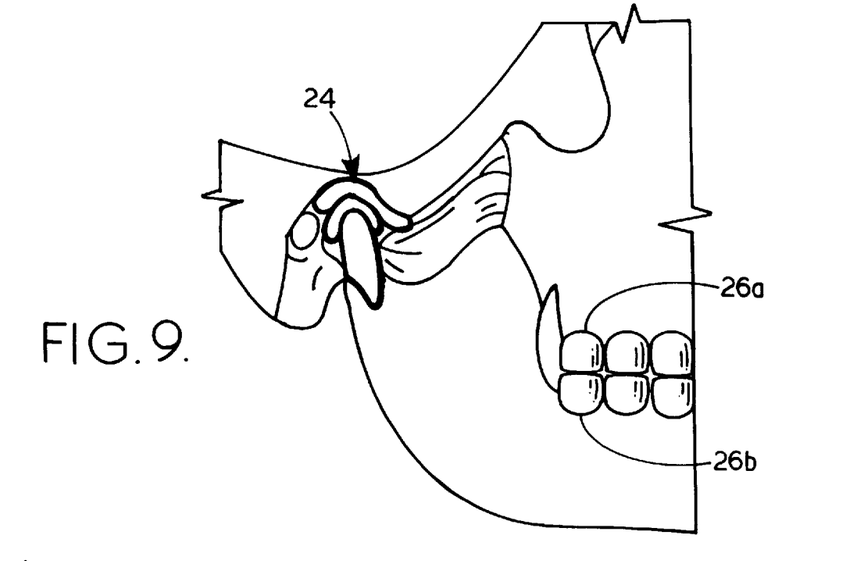
FIG. 9 is a side elevational view of a temporomandibular joint, shown with the teeth clenched.

FIG. 8a shows a modified form of a bitepad assembly 106 including a bitepad 120 with a modified configuration having a relatively narrow front end 120c, a relatively wide back end 120d and an inner edge 120e tapering therebetween. The modified bitepad assembly 106 provides an enlarged area at the bitepad back end 120d to provide greater contact area for the back teeth with the tapered inner edge thereof to facilitate ease of placement and retention in position. Such modified bitepad assemblies 106 can be used interchangeably with the bitepads 6.

Still further, the strap assembly 4 and the bitepad 6 can be formed integrally by molding or casting the mouthpiece 2 as a single article.

IV. Mouthpiece 2 Construction and Occlusal Support Method

The components of the mouthpiece 2 are preferably fabricated from a resilient, polymeric material from which the strap assembly 4 and the bitepad assemblies 6 can be stamped or otherwise formed. However, other manufacturing processes such as injection molding, vacuum forming, etc., can be utilized. The material comprising the strap assembly 4 is preferably flexible to accommodate forming in a desired U-shaped configuration to fit the teeth of a particular wearer.

For example, ethylene vinyl acetate (EVA) has been found to be a suitable material. However, other materials with the desired characteristics of resiliency, flexibility and durability may be utilized. Moreover, the hardness of the materials can be controlled to provide desired performance characteristics.

The material comprising the strap assembly 2 is preferably chosen to provide sufficient flexibility to accommodate the shape of a person's dental structure, and may include a certain amount of memory to maintain such a shape.

The strap assembly 2 and the bitepad assemblies 4 are preferably formed separating to facilitate manufacturing, adjustability and to minimize cost of manufacture. However, the strap and bitepad assemblies 4, 6 can be integrally formed. Moreover, the displacement of the bridge 10 from the line of the wings 14 can be varied to accommodate various wearers of the mouthpiece 2.

The material chosen for the mouthpiece 2 is preferably washable for purposes of cleaning same.

The adjustable mounting feature of the bitepad assemblies 4 enables the mouthpiece 2 to accommodate various wearers of various dental structures.

The appropriate receiver 18 is chosen to accommodate a pin subassembly 22 of each bitepad assembly 6. Thus, the outermost/rearmost receivers are preferably utilized by wearers with larger bites, whereas receivers 18 which are more closely/forwardly spaced are preferably utilized for wearers with smaller dental bites.

The bitepad assemblies 4 are mounted on the wings 14 by passing the balls 22b through respective receivers 18 whereby the shanks 22a are securely and rotatably retained within the receivers 18. The mouthpiece is placed in the mouth with the strap assembly 2 primarily encircling the front/outside portions of the jaw and lower teeth and with the strap inner face 4b placed against the lower teeth. The angular orientation of the bridge-to-extension and the extension-to-wing connections or joints 16a,b places the wings 14 at a level of the person's bite.

Figure 10:
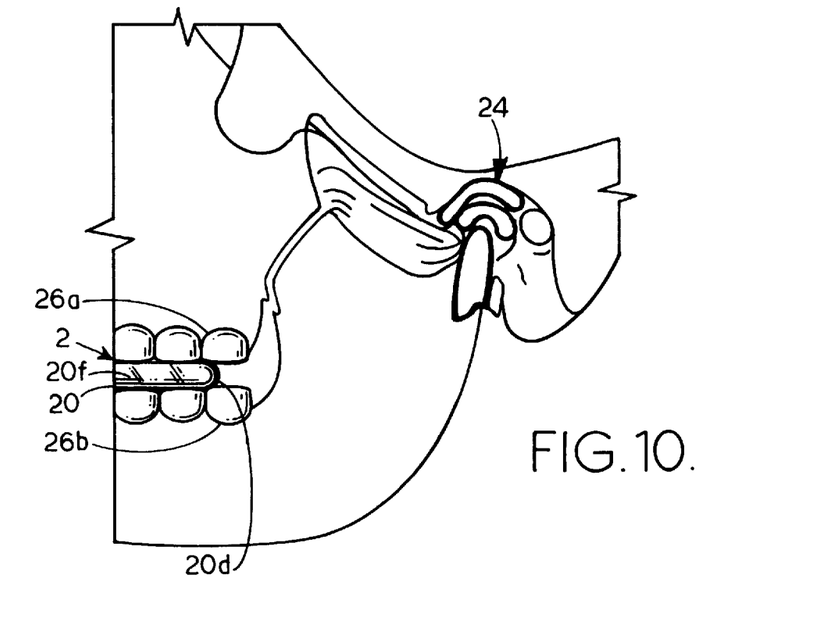
FIG. 10 is a side elevational view of the temporomandibular joint, shown with the teeth spaced by a mouthpiece embodying the present invention.

The bitepad assemblies 6 function to maintain a predetermined spacing of the back teeth 26a,b, while minimizing interference with other activities of the wearer, such as participation in physical sports, etc. The temporomandibular joint 24 is positioned in a manner as shown in FIG. 10 to provide both optimum bite control and a tension-free joint.

By eliminating the problems associated with bruxism, teeth grinding and teeth clenching, improved performance can be obtained in a variety of physical endeavors, such as sports, etc.

The configuration of the strap assembly 2 with its bridge and wings spaced with respect to each other minimizes interference from wearing the mouthpiece 2 which might otherwise interfere with talking, eating, breathing, etc. It will be appreciated that the mouthpiece 2 can be easily and quickly placed in position, removed and disassembled for cleaning. Moreover, the rotational connection of the bitepad assembly 6 to the wings 14 permits the strap assembly 4, and particularly the bridge 10, to be raised or lowered as desired for comfort and optimum performance. Due to the relatively compact configuration of the strap assembly 4, the mouthpiece 2 is barely noticeable to either a wearer or to others. By fabricating it of a relatively clear or translucent material, the mouthpiece 2 can be relatively effectively concealed. Moreover, since it is generally positioned on the lower teeth behind the lower lips, breathing is generally not impaired and an athlete can breath substantially as heavily as normal with the mouthpiece 2 in place.

The mouthpiece 2 can be customized. For example, excess length of the strap assembly 4 can be removed by cutting off the ends of the wings 14. Also, with suitable resins or other fabricating material, the strap assembly 4 could be heated and stretched.

The mouthpiece 2 can be easily disassembled for cleaning, storage, etc. Also, the mouthpiece 2 can be shipped and packaged in a disassembled condition to minimize the space required by same. The components of the mouthpiece 2 are generally reversible, i.e, the strap assembly 4 could be flipped over, as could the bitepad assemblies 6.

The spacing of the back teeth relieves tension from the temporomandibular joint for purposes of avoiding tension therein and the detrimental effects of bruxism (teeth grinding), teeth clenching, etc.

V. First Modified Embodiment Kinesiologic Mouthpiece 202

Figure 11:
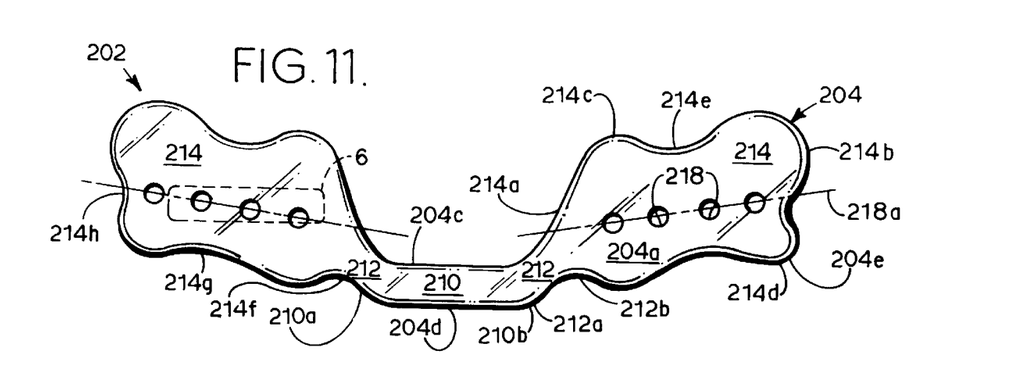
FIG. 11 is a front elevation of a strap assembly of a kinesiologic mouthpiece comprising a first modified embodiment of the present invention.

FIG. 11 shows a strap assembly 204 for a kinesiologic mouthpiece 202 comprising a modified embodiment of the present invention. The strap assembly 204 includes a first face 204a; a second face (not shown); upper and lower edges 204c,d and rounded corners 204e. The strap assembly 204 includes a bridge 210 with opposite sides 210a,b. A pair of extensions 212 each includes a front end 212a connected to a respective bridge side 210a,b and a back end 212b.

The strap assembly 204 includes a pair of wings 214 which are modified from the wings 14 described above. Each wing 214 includes a front end 214a connected to a respective extension back end 212b and a back end 214b. Each wing 214 also includes upper and lower edges 214c,d. Each wing upper edge 214c includes an upper recess 214e. Each wing lower edge 214d includes a lower front recess 214f located generally where the back end 212b of a respective extension 212 adjoins the front end 214a of a respective wing 214. Each wing lower edge 214d also includes a lower back recess 214g and each wing back end 214b includes a back end recess 214h. The recesses 214e–h all form gradual curves where they merge with respective wing edges 214c,d and wing back ends 214b.

Each wing 214 includes a plurality of receivers 218 (e.g. 4 are shown) which form a receiver line 218a. The receiver line 218a slopes downwardly from back-to-front whereby the frontmost receivers 218 are positioned at the lowest level, with each successive receiver 218 rearwardly being positioned at a slightly higher level than the proceeding one.

In operation, the greater overall heights of the wings 214 facilitate the proper positioning of the mouthpiece 202 and its retention in place. In particular, the greater heights of the wings 214 facilitate opening and closing the mouth while maintaining proper contact with the teeth and gums for retaining the mouthpiece 202 generally in a proper position. The strap assembly 204 can be provided with either bitepad assemblies 6 or bitepad assemblies 106 as described above, which can be attached in the same manner as described above. When the teeth are closed on the bitepads 6, the recesses 214e–h accommodate protrusions of the gums to provide a relatively comfortable fit. The downward slopes of the receiver line 218a function to adjust the overall proportions of the mouthpiece 202 for fit purposes whereby individuals with different sizes of mouths can be properly fitted by adjustably repositioning the bitepads 6. For example, with the bitepads 6 located in the frontmost receivers 218, a relatively small mouth could be accommodated, in which case it would probably be desirable to lower the positions of the bitepads 6 with respect to the bridge 10, which is accomplished automatically since the forwardmost receivers 218 are at the lowest receiver level.

VI. Second Modified Embodiment Kinesiologic Mouthpiece 302

Figure 12:
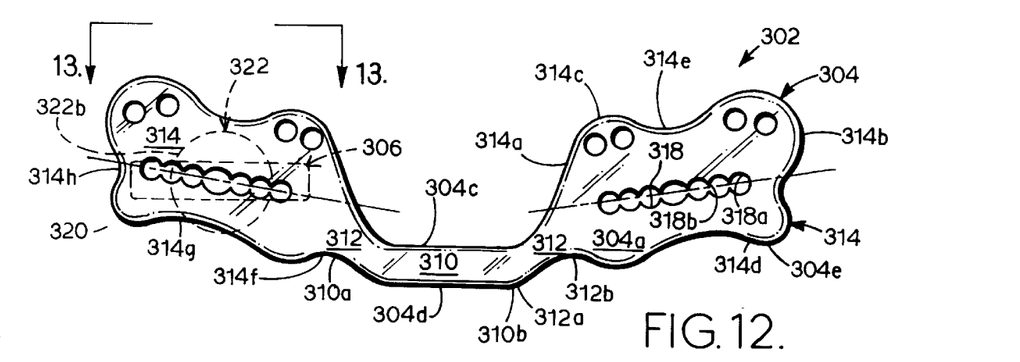
FIG. 12 is a front elevational view of a kinesiologic mouthpiece comprising a second modified embodiment of the present invention.
Figure 13:
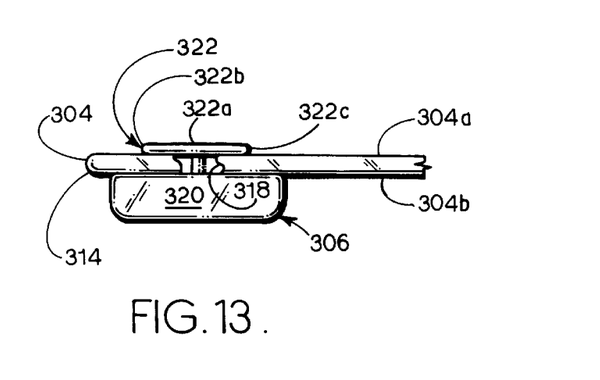
FIG. 13 is an enlarged, fragmentary, top plan view of the mouthpiece, particularly showing a bitepad assembly thereof.

FIGS. 12–13 show a kinesiologic mouthpiece 302 comprising a second modified embodiment of the present invention and including a strap assembly 304 mounting a pair of bitepad assemblies 306.

The strap assembly 304 includes a first face 304a; a second face 304b; upper and lower edges 304c,d and rounded corners 304e. Strap assembly 304 includes a bridge 310 with opposite sides 310a,b. A pair of extensions 312 each includes a front end 312a connected to a respective bridge side 310a,b and a back end 312b.

The strap assembly 304 includes a pair of wings 314 which are modified from the wings 14 and 214 described above. Each wing 314 includes a front end 314a connected to a respective extension back end 312b and a back end 314b. Each wing 314 also includes upper and lower edges 314c,d. Each wing upper edge 314c includes an upper recess 314e and each wing lower edge 314d includes a lower front recess 314f and a lower back recess 314g. Each wing back end 314b includes a back end recess 314h. A multi-position, multi-receiver slot 318 is formed in each wing 314 and comprises a series of interconnected receivers 318a with connecting passages 318b therebetween.

Each bitepad assembly 306 includes a bitepad 320 with a pin subassembly 322 comprising a shank 322a extending outwardly therefrom and mounting a flange 322b, which preferably is relatively thin and includes a rounded perimeter 322c. The relatively flat pin subassembly flange 322b provides user comfort since it protrudes only a short distance from the strap assembly first face 304a.

The second modified kinesiologic mouthpiece 302 is formed by inserting the flange 322b through the multi-position receiver slot 318 to a position where the wings 314 are captured between respective bitepads 320 and pin subassembly flanges 322b with pin subassembly shanks 322a extending through respective receiver slots 318. The passages 318b between the receivers 318a permit slidably repositioning the bitepad assemblies 306 on the wings 314. The bitepad assemblies 306 can thus be slid forward and back with their respective pin subassembly shanks 322a registering in respective receivers 318a. The multi-position, multi-receiver slots 318 thus provide a number of positions for the bitepad assembly 306 and facilitates relatively easy adjustment since the adjustments can be made without separating the bitepad assemblies 306 from the strap assembly 304.

Each wing 314 also includes a plurality of relief holes 324 which can be positioned, for example, in proximity to the wing upper edges 314c near the front and back ends 314f,g thereof. The relief holes 324 facilitate passage of saliva through the wings 314, and also increase the flexibility of the wings 314 in those areas.

The second modified embodiment kinesiologic mouthpiece 302 functions in a manner similar to the mouthpieces 2 and 202 described above, except that the positions of the bitepad assembly 306 can be adjusted without separating them from the strap assembly wings 314. Moreover, assembly can be simplified because the pin subassembly flanges 322b can be inserted through the multi-position receiver slots 318. The second modified embodiment kinesiologic mouthpiece 302 can thus be relatively easy to use, even for a person with reduced hand and finger capabilities, which can be associated with arthritis and other medical conditions.

It is to be understood that while certain forms of the present invention have been illustrated and described herein, it is not to be limited to the specific forms or arrangement of parts described and shown.

What is claimed and desired to be secured by Letters Patent is as follows:

1. A kinesiologic mouthpiece, which comprises:
   (a) a strap assembly including:
      (1) a bridge with opposite sides;
      (2) a pair of extensions each having a front end connected to a respective bridge side and a back end; and
      (3) a pair of wings each having a front end connected to a respective extension back end and a free wing back end;
   (b) a pair of bitepad assemblies each having:
      (1) a bitepad with upper and lower surfaces and inner and outer edges;
   (c) mounting means for mounting each said bitepad assembly on a respective wing with a respective bitepad outer edge against a respective wing;
   (d) each said wing having a receiver; and
   (e) each said bitepad assembly having a pin selectively receivable in said receiver.

2. The mouthpiece according to claim 1 wherein each said mounting means includes:
   (a) a plurality of receivers in each said wing, said receivers in each said wing being positioned in longitudinally-spaced relation.

3. The mouthpiece according to claim 2, which includes:
   a) the receivers in each said wing being generally aligned along an axis which slopes downwardly from back-to-front.

4. The mouthpiece according to claim 2, which includes:
   (a) said receivers in each said wing being positioned adjacent to each other; and
   (b) a plurality of passages in each said wing, each said passage interconnecting a respective, adjacent pair of said receivers.

5. The mouthpiece according to claim 1 wherein each said mounting means includes:
   (a) said pin means comprising a shank protruding from said bitepad outer edge; and
   (b) a ball mounted on said shank in spaced relation from said bitepad outer edge.

6. The mouthpiece according to claim 1, which includes:
   (a) each said extension extending upwardly and rearwardly from a respective bridge side.

7. The mouthpiece according to claim 1 wherein each said bitepad includes a pair of rounded, inner corners.

8. The mouthpiece according to claim 1 wherein each said bitepad includes radiused edges.

9. The mouthpiece according to claim 1 which comprises ethylene vinyl acetate.

10. The mouthpiece according to claim 1, which includes:
   a) each said wing having upper and lower edges; and
   b) each said upper and lower wing edge having a respective recess.

11. The mouthpiece according to claim 10, which includes:
   a) each said wing back end having a forwardly-extending, outwardly concave recess.

12. The mouthpiece according to claim 10, which includes:
   a) each said wing lower edge recess comprising a lower, back recess; and
   b) each said wing lower edge having a lower front recess in proximity to its front end whereat it connects to a respective bridge side.

13. The mouthpiece according to claim 1 wherein each said mounting means includes:
   (a) said pin means comprising a shank protruding from said bitepad outer edge; and
   (b) a generally circular flange mounted on said shank in spaced relation from said bitepad outer edge.

14. A kinesiologic mouthpiece, which comprises:
   (a) a strap assembly, which includes:
      (1) a bridge with opposite sides;
      (2) a pair of extensions each having a front end connected to a respective bridge side and a back end, each said extension forming an obtuse angle with respect to said bridge and extending generally rearwardly and upwardly from a respective bridge side;
      (3) a pair of wings each having a front end connected to a respective extension back end and a free back end;
      (4) said strap having inner and outer faces; and
      (5) said strap having upper and lower edges;
   (b) a pair of bitepad assemblies each including a bitepad with:
      (1) an upper contact surface;
      (2) a lower contact surface;
      (3) a front end;
      (4) a back end;
      (5) an inner edge; and
      (6) an outer edge; and
   (c) a pair of bitepad mounting means each including:
      (1) each said wing having a plurality of receivers positioned in longitudinally-spaced relation with said receivers being positioned along a receiver line located between and generally parallel to said strap edges at a respective wing;
      (2) a pair of pin subassemblies each including a shank connected to and extending outwardly from a respective bitepad outer edge and a ball mounted on the end of the shank; and
      (3) each said bitepad assembly having a plurality of positions in spaced relation from front-to-back with respect to a respective wing and with a pin subassembly thereof positioned in a respective wing receiver.

15. A kinesiologic mouthpiece, which comprises:
   (a) each said bitepad mounting means includes means for longitudinally, adjustably repositioning a respective bitepad on a respective wing;
   (b) a strap assembly including:
      (1) a bridge with opposite sides;
      (2) a pair of extensions each having a front end connected to a respective bridge side and a back end; and
      (3) a pair of wings each having a front end connected to a respective extension back end and a free wing back end;
   (c) a pair of bitepad assemblies each having:
      (1) a bitepad with upper and lower surfaces and inner and outer edges; and
   (d) mounting means for mounting each said bitepad assembly on a respective wing with a respective bitepad outer edge against a respective wing.

16. A kinesiologic mouthpiece, which comprises:
   (a) a front end;
   (b) a back end;
   (c) said bitepad front end being narrower than said bitepad back end;
   (d) said bitepad inner edges converging from back-to-front towards said bitepad outer edges respectively;
   (e) a strap assembly including:
      (1) a bridge with opposite sides;
      (2) a pair of extensions each having a front end connected to a respective bridge side and a back end; and
      (3) a pair of wings each having a front end connected to a respective extension back end and a free wing back end;
   (f) a pair of bitepad assemblies each having:
      (1) a bitepad with upper and lower surfaces and inner and outer edges; and
   (g) mounting means for mounting each said bitepad assembly on a respective wing with a respective bitepad outer edge against a respective wing.

17. A kinesiologic mouthpiece, which comprises:
   (a) said wing edge recess having a curved, outwardly concave configuration and merging with said wing lower edges along respective curves;
   (b) each said wing having upper and lower edges;
   (c) each said upper and lower wing edge having a respective recess;
   (d) a strap assembly including:
      (1) a bridge with opposite sides;
      (2) a pair of extensions each having a front end connected to a respective bridge side and a back end; and
      (3) a pair of wings each having a front end connected to a respective extension back end and a free wing back end;
   (e) a pair of bitepad assemblies each having:
      (1) a bitepad with upper and lower surfaces and inner and outer edges; and
   (f) mounting means for mounting each said bitepad assembly on a respective wing with a respective bitepad outer edge against a respective wing.

18. A method of controlling teeth spacing and temporomandibular joint orientation and providing occlusal support, which comprises the steps of:
   (a) adjusting the positions of the bitepads fore-and-aft with respect to the strap;
   (b) a strap assembly including:
      (1) a bridge with opposite sides;
      (2) a pair of extensions each having a front end connected to a respective bridge side and a back end; and
      (3) a pair of wings each having a front end connected to a respective extension back end and a free wing back end;

(c) a pair of bitepad assemblies each having:
   (1) a bitepad with upper and lower surfaces and inner and outer edges; and
(d) mounting means for mounting each said bitepad assembly on a respective wing with a respective bitepad outer edge against a respective wing.

19. A method of controlling teeth spacing and temporomandibular joint orientation and providing occlusal support, which comprises the steps of:
   (a) rotatably mounting said bitepads on said strap;
   (b) a strap assembly including:
      (1) a bridge with opposite sides;
      (2) a pair of extensions each having a front end connected to a respective bridge side and a back end; and
      (3) a pair of wings each having a front end connected to a respective extension back end and a free wing back end;
   (c) a pair of bitepad assemblies each having:
      (1) a bitepad with upper and lower surfaces and inner and outer edges; and
   (d) mounting means for mounting each said bitepad assembly on a respective wing with a respective bitepad outer edge against a respective wing.

20. A method of controlling teeth spacing and temporomandibular joint orientation and providing occlusal support, which comprises the steps of:
   (a) providing said strap with a bridge with opposite sides, a pair of extensions each having a front end connected to a respective bridge side and a back end and a pair of wings each having a front end connected to a respective extension back end and a back free end;
   (b) positioning said strap on the outside of the lower teeth;
   (c) positioning said bridge in spaced relation below a level of said wings;
   (d) extending each said extension upwardly and rearwardly from its front end to its back end;
   (e) mounting each said bitepad on a respective wing;
   (f) a strap assembly including:
      (1) a bridge with opposite sides;
      (2) a pair of extensions each having a front end connected to a respective bridge side and a back end; and
      (3) a pair of wings each having a front end connected to a respective extension back end and a free wing back end;
   (g) a pair of bitepad assemblies each having:
      (1) a bitepad with upper and lower surfaces and inner and outer edges; and
   (h) mounting means for mounting each said bitepad assembly on a respective wing with a respective bitepad outer edge against a respective wing.

* * * * *